United States Patent [19]

Jones et al.

[11] 4,069,321

[45] Jan. 17, 1978

[54] BLOCKED CHOLECALCIFEROL AND DIHYDROTACHYSTEROL 3 DERIVATIVES

[75] Inventors: Howard Jones, Holmdel; Shu Shu Yang, Piscataway; David P. Jacobus, Princeton, all of N.J.

[73] Assignee: Merck & Co., Inc., Rahway, N.J.

[21] Appl. No.: 722,443

[22] Filed: Sept. 13, 1976

Related U.S. Application Data

[63] Continuation-in-part of Ser. No. 621,976, Oct. 14, 1975.

[51] Int. Cl.² ............................ A61K 31/59; C07J 9/00
[52] U.S. Cl. ............................ 424/236; 260/239.55 R; 260/397.2
[58] Field of Search ........................................ 260/397.2

[56] References Cited

U.S. PATENT DOCUMENTS

| | | | |
|---|---|---|---|
| 2,862,934 | 12/1958 | Koevoet et al. | 260/397.2 |
| 3,607,888 | 9/1971 | DeLuca | 260/397.2 |
| 3,833,622 | 9/1974 | Babcock et al. | 260/397.2 |

Primary Examiner—Elbert L. Roberts
Attorney, Agent, or Firm—Rudolph J. Anderson, Jr.; Harry E. Westlake, Jr.; Frank M. Mahon

[57] ABSTRACT

Novel cholecalciferol and dihydrotachysterol$_3$ derivatives produced against metabolic conversions at the 25-position, their preparation, pharmaceutical compositions, methods of treating steroid-induced osteoporosis, senile osteoporosis and secondary hyperparathyroidism, especially that induced by an insufficient amount of calcium in relationship to the amount of phosphate, novel intermediates and their preparation are disclosed.

11 Claims, No Drawings

BLOCKED CHOLECALCIFEROL AND DIHYDROTACHYSTEROL 3 DERIVATIVES

This application is a continuation-in-part of prior co-pending application, U.S. Ser. No. 621,976, filed Oct. 14, 1975.

BACKGROUND OF THE INVENTION

Known vitamin D compounds, such as cholecalciferol and dihydrotachysterol$_3$ derivatives and metabolites thereof, promote both intestinal-calcium and phosphate transport and in conjunction with parathormone promote bone-calcium mobilization (bone resorbtion).

It is an object of the invention to find a class of novel cholecalciferol and dihydrotachysterol$_3$ derivatives which promote intestinal-calcium transport without the usual magnitude of bone-calcium mobilization, i.e. selectively promote intestinal transport, expecially calcium, as opposed to bone mobilization. This differential effect has been widely sought for treatment of steroid-induced osteoporosis, senile osteoporosis and secondary hyperparathyroidism, especially that induced by an insufficient amount of calcium in relationship to the amount of phosphate.

DETAILED DESCRIPTION

We have found that cholecalciferol and dihydrotachysterol$_3$ and their derivatives may be metabolically blocked by the presence of a halo or O–C$_{1-5}$ alkyl carbamate group in the 25-position. These compounds may also be metabolically blocked in the 3- and/or 24-positions, in addition to the 25-position, with either a halo or O–C$_{1-5}$ alkyl carbamate group. The presence of one or more of the groups listed above retards metabolic hydroxylation in vivo in the blocked position(s). These novel metabolically blocked compounds promote intestinal-calcium transport as opposed to bone-calcium mobilization. The novel metabolically-blocked cholecalciferol and dihydrotachysterol$_3$ compounds of this invention have the following structural formulae:

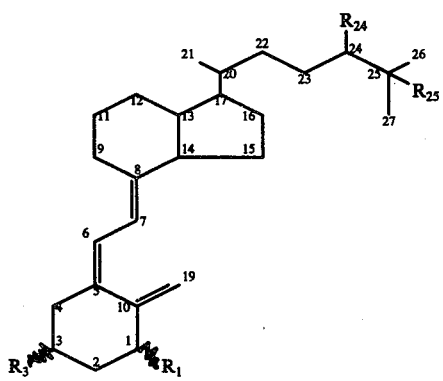

and

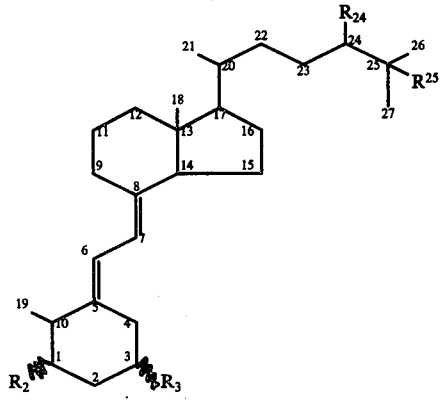

wherein:

R$_1$, is hydrogen, hydroxy, C$_{1-5}$alkanoyloxy, such as acetoxy or propionyloxy, substituted C$_{1-5}$alkanoyloxy, such as haloC$_{1-5}$alkanoyloxy (bromoacetoxy) or branchedC$_{3-5}$alkanoyloxy (isopropionyloxy), benzoyloxy or substituted benzoyloxy, such as p-nitrobenzoyloxy, R$_3$, R$_{24}$ and R$_{25}$ are hydrogen, hydroxy, C$_{1-5}$alkanoyloxy, such as acetoxy or propionyloxy, substituted C$_{1-5}$alkanoyloxy, such as haloC$_{1-5}$alkanoyloxy (bromoacetoxy) or branchedC$_{3-5}$alkanoyloxy (isopropionyloxy), benzoyloxy, substituted benzoyloxy, such as p-nitrobenzoyloxy, halo, such as chloro, bromo, iodo and especially fluoro or O—C$_{1-5}$alkyl carbamate, such as O-methyl carbamate, O-ethyl carbamate or O-isopropyl carbamate with the proviso that R$_{25}$ must be halo or O—C$_{1-5}$alkyl carbamate. O—C$_{1-5}$Alkyl carbamates have the following structure:

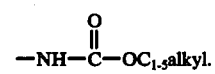

In a preferred embodiment, R$_1$, R$_3$ and R$_{24}$ are hydrogen or hydroxy.

In a more preferred embodiment, R$_{25}$ is fluoro.

The novel compounds of formula I are named as derivatives of cholecalciferol. Cholecalciferol is also known as vitamin D$_3$, activated 7-dehydrocholesterol and 9,10-seco-5,7,10(19)-cholestatrien-3β-ol. The novel compounds of formula IA are named as derivatives of dihydrotachysterol$_3$. The following novel compounds are representative of this invention:

25-Fluorocholecalciferol,
25-Fluoro-9,10-dihydrotachysterol$_3$,
25-Fluoro-1α-hydroxycholecalciferol,
25-Fluoro-1α-hydroxy-9,10-dihydrotachysterol$_3$,
25-Fluoro-1α-hydroxy-3-desoxycholecalciferol,
3β,25-Difluoro-1α-hydroxy-3-desoxycholecalciferol,
24,25-Difluorocholecalciferol,
24,25-Difluoro-9,10-dihydrotachysterol$_3$,
24,25-Difluoro-1α-hydroxycholecalciferol,
24,25-Difluoro-1α-hydroxy-9,10-dihydrotachysterol$_3$,
25-Fluoro-1α,24-dihydroxycholecalciferol,
25-Fluoro-1α,24-dihydroxy-3-desoxycholecalciferol,
O-Methyl cholecalciferol-25-carbamate, and
O-Methyl 9,10-dihydrotachysterol-25-carbamate.

Another aspect of this invention relates to the novel pharmaceutical compositions for treating steroid-induced osteoporosis, senile osteoporosis and secondary hyperparathyroidism, especially that induced by an insufficient amount of calcium in relationship to the amount of phosphate, comprising a non-toxic pharmaceutically acceptable carrier and a compound of formulae I and IA, supra, wherein $R_1$, $R_3$, $R_{24}$ and $R_{25}$ are as defined above.

The non-toxic pharmaceutical carrier may be, for example, either a solid or a liquid. Exemplary of solid carriers are lactose, corn starch, gelatin, talc, sterotix, stearic acid, magnesium stearate, terra alba, sucrose, agar, pectin and acacia. Exemplary of liquid carriers are peanut oil, olive oil, sesame oil and water. Similarly, the carrier or diluent may include a time delay material such as glyceryl monostearate or glyceryl distearate, alone, or with a wax.

The treatment of steroid-induced osteoporosis, senile osteoporosis and secondary hyperparathyroidism, in accordance with the method of the present invention is accomplished by orally or parenterally administering to patients a compound of formulae I and IA, supra, or mixtures thereof in a non-toxic pharmaceutically acceptable carrier.

Several pharmaceutical forms of the therapeutically useful compositions may be used. For example, if a solid carrier is used, the compositions may take the form of tablets, capsules, powders, troches or lozenges, prepared by standard pharmaceutical techniques. If a liquid carrier is used, the preparation may be in the form of a soft gelatin capsule, a syrup, a liquid solution, a liquid emulsion or a liquid suspension.

The active compounds of formulae I and IA, supra, are administered in a therapeutically effective amount sufficient to treat steroid-induced osteoporosis, senile osteoporosis and secondary hyperparathyroidism. The metabolically blocked cholecalciferol derivatives will reduce the bone mobilization in those cases wherein clinical symptoms have not been observed, e.g. administered prophylactically to persons subject to steroid induced osteoporosis, and in addition retard bone mobilization in those cases wherein clinical symptoms have been observed, e.g. senile osteoporosis and secondary hyperparathyroidism. Advantageously, the active compounds of formulae I and IA, supra, will be administered, alone or in a pharmaceutical composition in an amount of from about 1.0 to 3000 International Units (IU) per day, preferably from about 10 to 500 IU/day. Standard preparations of vitamin $D_3$ have an activity of about 40 IU/$\mu$g. The daily dosage may be given either in single or multiple dosages.

The method of treatment of this invention comprises administering to a patient (animal or human) the compound of formulae I and IA, supra, as previously described admixed with a non-toxic pharmaceutical carrier such as exemplified above. It should be understood that although preferred dosage ranges are given, the dose level for any particular patient depends upon the activity of the specific compound employed. Also, many other factors that modify the actions of drugs will be taken into account by those skilled in the art in the therapeutical use of medicinal agents, particularly those described above; for example, body weight, sex, diet, time of administration, route or administration, rate of excretion, drug combination, reaction sensitivities and severity of the particular disease.

Another aspect of this invention relates to the novel intermediate compounds of formulae II, III, IV and V. Compounds II, III, IV and V are illustrated by the following flow sheet which also illustrates processes A, B and C for preparing compounds II, III and IV, wherein $R_1$, $R_3$, $R_{24}$ and $R_{25}$ are as defined above and X is chloro, bromo or iodo.

The novel process for preparing compounds of formulae I and IA forms another aspect of this invention. The compounds of formulae I and IA may be produced by isomerizing an O-blocked or non-O-blocked compound of formula II to give the corresponding O-blocked or non-O-blocked compound of formulae I and IA, or alternatively by un-O-blocking a O-blocked compound of formulae I and IA. The preferred compounds are the non-O-blocked compounds of formulae I and IA. The preferred process for producing these compounds is by isomerizing the previously un-O-blocked compound of formula II or un-O-blocking an O-blocked compound of formulae I and IA.

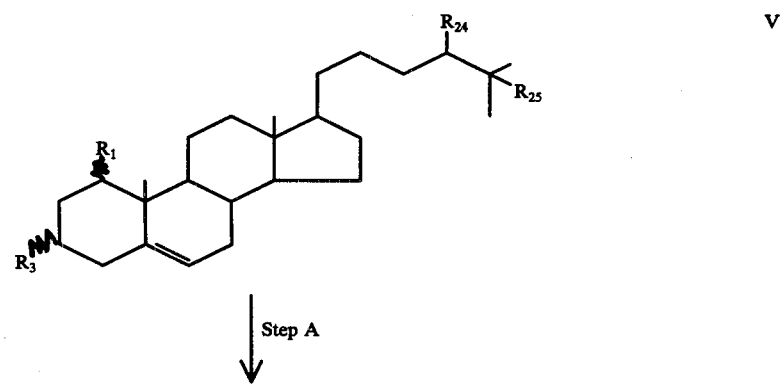

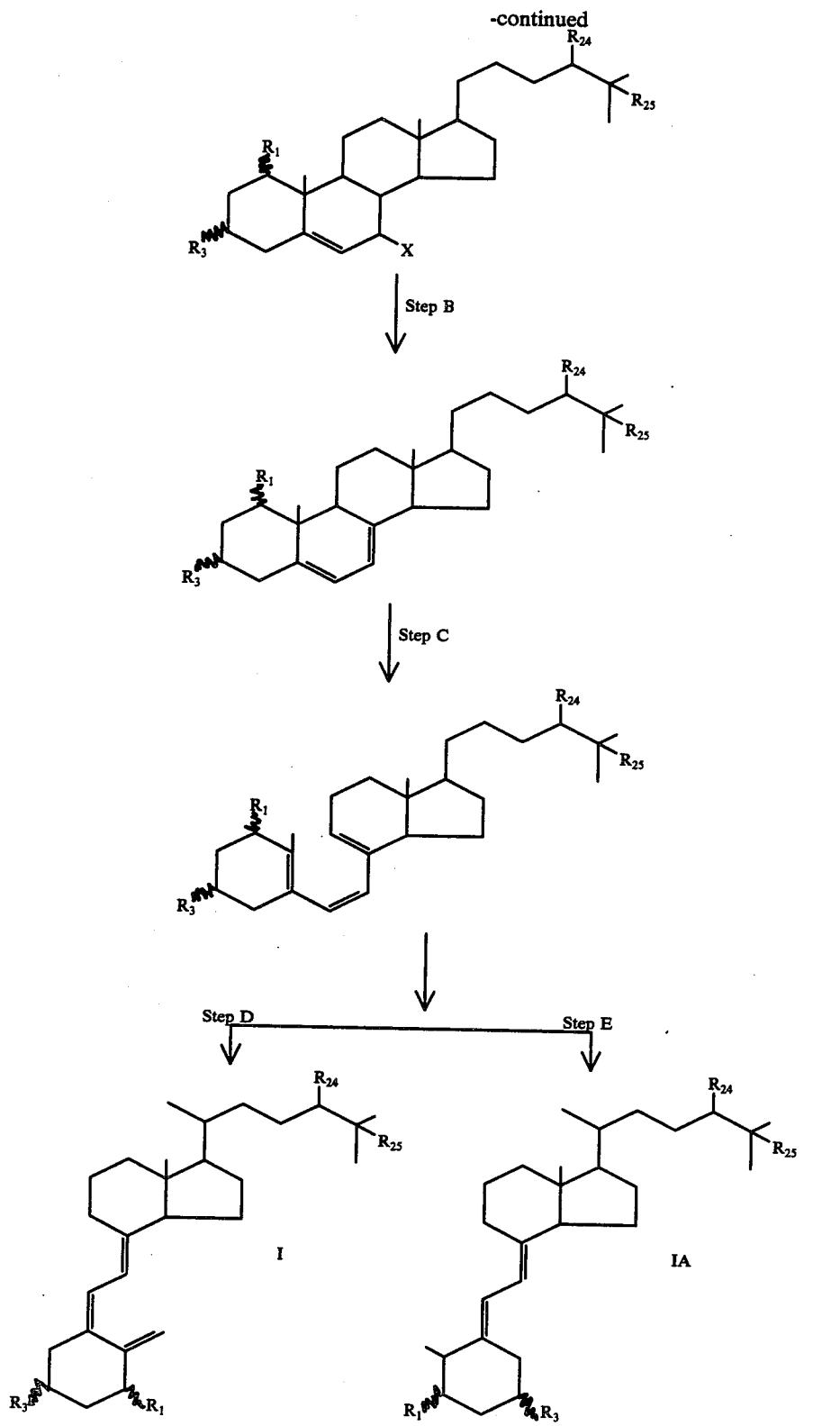

Preliminary Step — O-Blocking the Hydroxy Groups

The hydroxy groups, if present, of the compounds of formula V may be protected, if desired, by an $C_{1-5}$-alkanoyl group, such as formyl, acetyl or propionyl, substituted $C_{1-5}$-alkanoyl, branched $C_{1-5}$-alkanoyl, benzoyl or substituted benzoyl group, to form a simple ester with the hydroxy group(s) of formula V. The simple esters may be prepared from the corresponding acid, acid halide or anhydride of the $C_{1-5}$-alkanoyl or benzoyl group in the presence of a mild base.

Step A — Halogenation of the 7-Position

The compounds of formula V may be halogenated in the 7-position with a chloro, bromo or iodo group using a suitable halogenating agent under free radical halogenation conditions to produce a compound of formula IV.

Step B — Introduction of the Double Bond at the 7,8-Position by Dehydrohalogenation The compounds of formula IV may be dehydrohalogenated in the 7,8-position by treatment with a suitable dehydrohalogenation reagent neat, or in an inert solvent to produce a compound of formula III.

Step C — Irradiation of the Steroid Precursor to Produce the 9,10-Secosteroid The compound of formula III may be irradiated in a suitable inert solvent to produce the 9,10-secosteroid of formula II.

Step D — Isomerization of the 9,10-secosteroid to Produce the cholecalciferol and dihydrotachysterol$_3$ The compounds of formula II may be isomerized by dissolving them in a suitable solvent to produce the cholecalciferol structure of formula I. Suitable solvents include $C_{6-10}$alkanes, such as isooctane, and $C_{6-8}$ aromatic hydrocarbons, such as benzene, toluene and o-,m- or p-xylene. The reaction temperature is not critical and generally the isomerization is carried out at a temperature of from about 20° to 100° C., preferably at about 75° C. for about 2 hours. The time of reaction is not critical and generally the isomerization is carried out until the reaction is essentially complete. For example, at 75° 1 C. about 2 hours are required, whereas at 20° C. (room temperature about 14 days are required. The pressure is not critical and the isomerization is generally carried out at atmospheric pressure in an open system. A protective blanket of an inert gas, such as nitrogen or argon, is preferred. The product of the isomerization, compounds of formula I, may be recovered in a conventional manner, such as by evaporation of the solvent to yield the compound of formula I. The compound of formula I may be purified by chromatographing it on a silica gel column using a solvent system such as diethyl ether and petroleum ether.

Step E

The compounds of formula II also may be isomerized by dissolving them in a suitable solvent, such as those mentioned above, and treating them with iodine to produce the corresponding tachysterol$_3$ derivative which then is reduced to the desired dihydrotachysterol$_3$ derivatives of formula IA. The isomeration is run in the cold ($-10°$ to $10°$ C.) under an inert atmosphere such as nitrogen. Upon warming to room temperature, the solvent is removed to obtain the tachysterol$_3$ product.

Reduction to the dihydrotachysterol$_3$ products of formula IA may be carried out by adding the tachysterol$_3$ from the isomerization reaction to a refluxing mixture of sodium metal in a suitable solvent such as xylene and treating the resulting mixture with t-amyl alcohol. After cooling, the solvent may be removed in vacuo and the residue extracted with 50% ether-water mixture. The ether layer is concentrated in vacuo and the 9,10-dihydrotachysterol$_3$ product may be purified by preparative thin layer chromatography.

Post Step — Unblocking of O-Blocked Derivatives to Produce Cholecalciferol and Dihydrotachysterol$_3$ Derivatives The O-blocked compounds of formulae I and IA may be un-O-blocked, if desired, to produce cholecalciferol and dihydrotachysterol$_3$ derivatives of formulae I and IA. The unblocking may be accomplished by hydrolyzing the compound of formulae I and IA under acidic or basic conditions in a solvent. The solvent is not critical. Examples of suitable solvents are $C_{1-3}$alkanols, such as methanol, ethanol or isopropanol. The acidic or basic conditions may be produced by any inert acid or base. Examples of suitable acids are organic acids, such as p-toluenesulponic acid, and inorganic acids, such as hydrochloric acid, phosphoric acid and sulfuric acid. Examples of suitable bases are organic bases, such as tertiary amines (trimethylamine) and pyridines (pyridine, collidine), and inorganic bases, such as alkali metal hydroxides (potassium hydroxide, sodium hydroxide), alkali metal carbonates (sodium carbonate) or alkali metal bicarbonates (sodium bicarbonate). It is preferred to use a dilute acidic solvent of about 1.0 to 5.0 N, which may be prepared by adding a dilute aqueous acidic solution to the solvent. The unblocking of compounds of formulae I and IA may also be carried out by using lithium aluminum hydride in a suitable solvent such as diethyl ether or tetrahydrofuran to produce the compounds of formulae I and Ia and the corresponding alcohol of the organic acid used to block the precursor steroid compound in the Preliminary Step above. The reaction temperature is not critical and generally the unblocking is carried out at a temperature of about 20° to 150° C., preferably at room temperature. The time of reaction is not critical and generally the unblocking is carried out until the reaction is substantially complete. The pressure is not critical and the unblocking is generally carried out at atmospheric pressure in an open system. A protective blanket of an inert gas, such as nitrogen or argon, is preferred. The product of the unblocking, compounds of the formulae I and IA may be recovered in a conventional manner, such as by solvent extraction and removal of the solvent by evaporation to yield the crude compounds of formulae I and IA. The compound of formulae I and IA may be purified by chromatographing it on a silica gel column using a solvent system such as diethyl ether and petroleum ether.

Another aspect of this invention is the novel intermediate compounds of formula VI

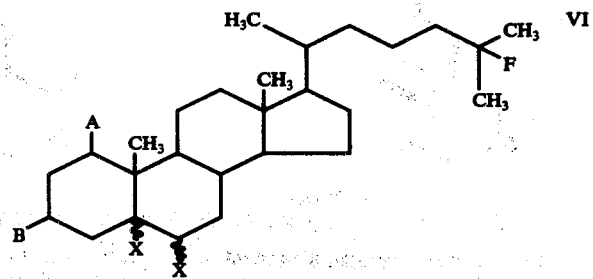

wherein
A and B are hydrogen, fluoro, $C_{1-5}$alkanoyloxy, such as acetoxy or propionyloxy, substituted $C_{1-5}$alkanoyloxy, such as haloC$_{1-5}$alkanoyloxy (bromoacetoxy) or branchedC$_{3-5}$alkanoyloxy (isopropionyloxy), benzoyloxy or substituted benzoyloxy, such as p-nitrobenzoyloxy, with the proviso that A may not be fluoro, and X is as defined above. The compounds of formula VI are dehalogenated in the 5 and 6 positions to produce compounds of formula V.

In a preferred embodiment, A and B are hydrogen, fluoro or C$_{1-5}$alkanoyloxy and X is bromo.

The following novel intermediate compounds are representative of compounds of formula VI:

5,6-Dibromo-25-fluorocholesteryl acetate,
1α-Acetoxy-5,6-dibromo-25-fluorocholesteryl acetate,
1α-Acetoxy-5,6-dibromo-3,25-difluorocholestane,
5,6-Dichloro-25-fluorocholesteryl acetate,
5,6-Diiodo-25-fluorocholesteryl acetate, and
5,6-Dibromo-3,25-difluorocholestane.

EXAMPLE 1

25-Fluoro-1α-hydroxycholecalciferol

A. 25-Fluorocholesteryl-3β-acetate

25-Hydroxycholesteryl-3β-acetate (0.01 moles) is dissolved in 100 mls of tetrahydrofuran and fluorinated by adding 2-chloro-1,1,2-trifluorotriethylamine (0.01 moles) with stirring at room temperature over a period of 10 minutes. The solvent is removed by evaporation and 25-fluorocholesteryl-3β-acetate is obtained. 25-fluorocholesteryl-3β-acetate can be purified by chromatographing the crude product on a silica gel column using a solvent of petroleum ether and diethyl ether.

B. 25-Fluorocholesterol

25-Fluorocholesteryl-3β-acetate (0.01 moles) prepared according to 1A above is saponified in 100 ml of ethanol containing 10% of a saturated aqueous potassium hydroxide solution. The mixture is refluxed for 30 minutes, cooled and extracted twice with 50 ml of chloroform. The chloroform extracts are washed with water, dried with magnesium sulfate and filtered. The solvent is removed by evaporation and crude 25-fluorocholesterol is obtained. 25-Fluorocholesterol can be purified by chromatographing the crude product on a silica gel column using a solvent of petroleum ether and diethyl ether.

C. 25-Fluoro-1,4,6-cholestatrien-3-one

25-Fluorocholesterol (0.01 moles) prepared according to 1B above is dissolved in 200 ml of dioxane and converted to the trienone by adding 2,3-dichloro-5,6-dicyanobenzoquinone (0.03 moles) with stirring at the reflux temperature over a period of 10 minutes. The mixture is refluxed for 30 hours and cooled to room temperature. The reaction mixture is filtered through neutral alumina and the solvent is removed by evaporation and crude 25-fluoro-1,4,6-cholestatatrien-3-one is obtained. 25-Fluoro-1,4,6-cholestatrien-3-one can be purified by chromatographing the crude product on a silica gel column using a solvent of petroleum and diethyl ether.

D. 1,2-Epoxy-25-fluoro-4,6-cholestadien-3-one

25-Fluoro-1,4,6-cholestatrien-3-one (0.01 moles) prepared according to 1C above is dissolved in 200 ml. of p-dioxane and 50 ml. of 1N-sodium hydroxide is added. The mixture is epoxidized by adding 17 ml. of a 30% solution of hydrogen peroxide with stirring over a period of 1 hour at room temperature. Stirring is continued for 20 hours at room temperature after which time the reaction mixture is diluted with 100 ml. of water and shaken with 200 ml. of ether. The ether layer is separated and washed with 50 ml. of water. The combined water phases are extracted twice with 50 ml. of ether. The two ether extracts are combined and washed with 50 ml. of water. The solvent is removed by evaporation to yield crude 1,2-epoxy-25-fluoro-4,6-cholestadien-3-one. 1,2-Epoxy-25-fluoro-4,6-cholestadien-3-one can be purified by chromatographing the crude product on a silica gel column using a solvent of petroleum ether and diethyl ether.

E. 25-Fluoro-1α-hydroxycholesterol 1,2-Epoxy-25-fluoro-4,6-cholestadien-3-one (0.01 moles) prepared according to 1D above is dissolved in 100 ml. of a 1:1 solvent mixture of tetrahydrofuran and liquid ammonia containing 0.04 moles of ammonium chloride. The mixture is stirred at reflux using a dry ice condenser and reduced by adding 0.42 grams of finally divided metalic lithium (0.06 gm. atoms) over a period of 10 minutes. The mixture is refluxed for one hour after which time the ammonia is allowed to evaporate from the mixture. The solvent is removed from the remainder of the mixture by evaporation to near dryness at room temperature. The residue is washed in 50 ml of ice water containing 5.0 g of ammonium chloride. The ice water is extracted three times with 50 ml of chloroform. The chloroform extracts are combined and the solvent is removed by evaporation to yield crude 25-fluoro-1α-hydroxycholesterol. 25-Fluoro-1α-hydroxycholesterol can be purified by chromatographing the crude product on a silica gel column using a solvent of petroleum ether and diethyl ether.

F. 1α-Acetoxy-25-fluorocholesteryl acetate

25-Fluoro-1α-hydroxycholesterol (0.01 moles) prepared according to 1E above is acetylated by dissolving the compound in 100 ml of acetic anhydride and 10 ml of pyridine. The acetylation mixture is maintained at 40° C for 48 hours. The reaction mixture is allowed to cool to room temperature and extracted with diethyl ether and water (pH 4 with sulfuric acid). The ether phase is collected and the aqueous phase is extracted twice with diethyl ether. The ether phases are combined and the solvent is removed by evaporation to yield crude 25-fluoro-1α-acetoxycholesteryl acetate. 25-Fluoro-1α-acetoxycholesteryl acetate can be purified by chromatographing the crude product on a silica gel column using a solvent of petroleum ether and diethyl ether.

G. 1α-Acetoxy-7-bromo-25-fluorocholesteryl acetate

25-Fluoro-1α-acetoxycholesteryl acetate (0.01 moles) prepared according to 1F above is dissolved in 100 ml of hexane and placed in a 72° C water bath and brominated by adding 0.005 moles of N,N'-dibromodimethylhydantoin. The reaction mixture is stirred for 10 minutes and placed in an ice bath for 2 minutes. The reaction mixture is filtered, the filtrate is collected and the precipitate is washed twice with 5 ml of cold hexane. The filtrate and washings are combined and the solvent is removed by evaporation to yield crude 1α-acetoxy-7-bromo-25-fluorocholesteryl acetate. 1α-Acetoxy-7-bromo-25-fluorocholesteryl acetate can be purified by chromatographing the crude product on a silica gel column using a solvent of petroleum ether and diethyl ether.

H. 1α-Acetoxy-7-dehydro-25-fluorocholesteryl acetate

1α-Acetoxy-7-bromo-25-fluorocholesteryl acetate (0.01 moles) prepared according to 1G above is dissolved in 50 ml of xylene and dehydrobrominated by adding to a solution containing 0.015 moles of trimethyl phosphite in 40 ml of xylene at 135° C over a period of 10 minutes under a blanket of nitrogen. The reaction mixture is maintained at 135° C for 90 minutes. The reaction mixture is allowed to cool to room temperature and the solvent is removed by evaporation to yield crude 1α-acetoxy-7-dehydro-25-fluorocholesteryl acetate. 1α-Acetoxy-7-dehydro-25-fluorocholesteryl acetate can be purified by chromatographing the crude product on a silica gel column using a solvent of petroleum ether and diethyl ether.

I. 1α-Acetoxy-25-fluoro-5(10),6,8-trienyl-9,10-secocholesteryl acetate

1α-Acetoxy-7-dehydro-25-fluorocholesteryl acetate (0.01 millimoles) prepared according to 1H above is dissolved in 800 ml of diethyl ether and irradiated by exposing the solution to the radiation from a Hanovia high pressure quartz mercury vapor lamp (Model 654A) for one minute under a blanket of nitrogen in a double-walled water cooled quartz emersion well. During irradiation the ether solution is stirred vigorously and continuously flushed with nitrogen. The solvent is removed by evaporation to yield a residue of starting material and 1α-acetoxy-25-fluoro-5(10),6,8-trienyl-9,10-seco-cholesteryl acetate. 1α-Acetoxy-25-fluoro-5(10),6,8-trienyl-9,10-secocholesteryl acetate can be separated from the starting material by chromatographing the residue on a silver nitrate impregnated silica gel column using a solvent of petroleum ether and diethyl ether.

J. 1α-Acetoxy-25-fluorocholecalciferol acetate

1α-Acetoxy-25-fluoro-5(10),6,8-trienyl-9,10-secocholesteryl acetate (0.01 moles) prepared according to 1I above is dissolved in 100 ml of isooctane and isomerized by heating the solution at 75° C under a nitrogen atmosphere for two hours. The solution is allowed to cool to room temperature and the solvent is removed by evaporation to yield 1α-acetoxy-25-fluorocholecalciferol acetate. 1α-Acetoxy-25-fluorocholecalciferol acetate can be purified by chromatographing the residue on a silica gel column using a solvent of petroleum ether and diethyl ether.

K. 25-Fluoro-1α-hydroxycholecalciferol

1α-Acetoxy-25-fluorocholecalciferol acetate (0.01 moles) prepared according to 1J above is saponified by dissolving in 200 ml. of methanol containing of 5% of a saturated aqueous potassium hydroxide solution at room temperature under a nitrogen atmosphere for 16 hours. The reaction is extracted with water and chloroform. The chloroform layer is collected, washed with water, dried with magnesium sulfate and evaporated to dryness leaving a residue of 25-fluoro-1α-hydroxycholecalciferol. 25-Fluoro-1α-hydroxycholecalciferol can be recrystallized from a mixture of petroleum ether and diethyl ether.

EXAMPLE 2

25-Fluorocholecalciferol

A. 25-Fluorocholestryl-3β-acetate

To 234 mg. of 25-hydroxycholestryl-3-acetate in 25ml. of methylene chloride, add 5 ml. of TRI-SIL reagent and stir at ambient temperature for 15 minutes. Add 0.3 ml. of phenyltetrafluorophosphorane followed by another 0.2 ml. after 5 minutes. Stir at room temperature for 1 hour. Add 3 gm. silica gel to the reaction mixture then concentrate in vacuo. Chromatograph residue on 50 gm. of silica gel. Elute with 25 to 50% benzene-petroleum ether. Remove the solvent to give the title compound.

B. 25-Fluorocholecalciferol

25-Fluorocholesteryl acetate, prepared according to A above is brominated using the procedure of 1G above to produce 7-bromo-25-fluorocholesteryl acetate; 7-bromo-25-fluorocholesteryl acetate is dehydrobrominated using the procedure of 1H above to produce 3β-acetoxy-25-fluoro-5,7-cholestadiene; 3β-aceotxy-25-fluoro-5,7-cholestadiene is irradiated using the procedure of 1I above to produce 25-fluoro-5(10),6,8-trienyl-9,10-secocholesteryl acetate; 25-fluoro-5(10),6,8-trienyl-9,10-secocholesteryl acetate is isomerized using the procedure of 1J above to produce 25-fluorocholecalciferol acetate; 25-fluorocholecalciferol acetate is saponified using the procedure of 1K above to produce 25-fluorocholecalciferol.

The TRI-SIL reagent employed in Step A above is a mixture of hexamethyldisilazane and chlorotrimethyl-/silane in pyridine and is available commercially from Pierce Chemical Company, Rockford, Ill.

EXAMPLE 3

25-Fluoro-1α-hydroxy-3-desoxycholecalciferol

A. 1,2-Epoxy-25-fluoro-4,6-cholestadien-3-one

25-Fluorocholesteryl acetate prepared according to 2A above is seaponified using the procedure of 1B above to produce 25-fluorocholesterol; 25-fluorocholesterol is converted to the trienone using the procedure of 1C above to produce 25-fluoro-1,4,6-cholestatrien-3-one; and 25-fluoro-1,4,6-cholestatrien-3-one is epoxidized using the procedure of 1D above to produce 1,2-epoxy-25-fluoro-4,6-cholestadien-3-one.

B. 25-Fluoro-4,6-cholestadiene-1α,3β-diol 1,2-Epoxy-25-fluorocholestadien-3-one (0.01 mole) prepared according to 3A above is dissolved in 100 ml. of dry tetrahydrofuran under a nitrogen blanket at 0° C. and fresh lithium aluminum hydride (0.005 mole) is slowly added over 10 minutes with stirring. The mixture is stirred for 1.0 hour and 1.0 ml. of ethyl acetate is added to destroy the excess lithium aluminum hydride. Concentrated aqueous ammonium chloride (20 ml.) is added to the reaction mixture and the mixture is stirred for 5 minutes. Diethyl ether (200 ml.) is added to the reaction mixture, the mixture is well shaken and the organic layer separated. The organic layer is washed with water, dried with magnesium sulfate and the solvent is evaporated to give crude 25-fluoro-4,6-cholestadiene-1α,3β-diol. 25-Fluoro-4,6-cholestadiene-1α,3β-diol can be purified by chromatographing the crude product on a silica gel column using a solvent of petroleum ether and diethyl ether.

C. 25-Fluoro-1α-hydroxycholest-5-ene

25-Fluoro-4,6-cholestadiene-1α,3β-diol (0.005 mole) prepared according to 3B above is dissolved in 100 ml. of a 1:1 solvent mixture of tetrahydrofuran and liquid ammonia and stirred at reflux using a dry-ice condenser with 0.4 gm. of finely divided lithium for 1.0 hour. The liquid ammonia is allowed to evaporate and 10 ml. of water is added. The tetrahydrofuran is evaporated at room temperature under high vacuum. The organics are extracted from the water three times with 50 ml. of chloroform. The chloroform extracts are combined, dried (magnesium sulfate) and the solvent is removed to give crude 25-fluoro-1α-hydroxycholest-5-ene. 25-

Fluoro-1α-hydroxycholest-5-ene can be purified by chromatographing the crude product on a silica gel column using a solvent of petroleum ether and diethyl ether.

D. 25-Fluoro-1α-hydroxy-3-desoxycholecalciferol

25-Fluoro-1α-hydroxycholest-5-ene, prepared according to 3C above, is acetylated using the procedure of 1F above to produce 1α-acetoxy-25-fluorocholest-5-ene; 1α-acetoxy-25-fluorocholest-5-ene is brominiated using the procedure of 1G above to produce 1α-aceotxy-7-bromo-25-fluorocholest-5-ene; 1α-acetoxy-7-bromo-25-fluorocholest-5-ene is dehydrobrominated using the procedure of 1H above to produce 1α-acetoxy-5,7-cholestadiene; 1α-acetoxy-25-fluoro-5,7-cholestadiene is irradiated using the procedure of 1I above to produce 25-fluoro-5(10),6,8-trienyl-9,10-seco-cholesten-1α-acetate; 25-fluoro-5(10),6,8-trienyl-9,10-secocholesten-1α-acetate is isomerized using the procedure of 1J above to produce 1α-acetoxy-25-fluoro-3-desoxycholecalciferol; and 1α-acetoxy-25-fluoro-3-desoxycholecalciferol is saponified using the procedure of 1K above to produce 25-fluoro-1α-hydroxy-3-desoxycholecalciferol.

EXAMPLE 4

3β,25-Difluoro-1α-hydroxy-3-desoxycholecalciferol

A. 25-Fluoro-1α-hydroxycholesteryl-3-tosylate and 25-fluoro-1α-tosylcholesterol

25-Fluoro-1α-hydroxycholesterol (0.005 moles) prepared according to 1E above, is stirred in 50 ml of dry pyridine under a nitrogen blanket and freshly crystallized, dry p-toluenesulfonyl chloride (0.006 moles) is added in 15 ml of pyridine over a period of 10 minutes at 0° C. After stirring for 1.0 hour, the reaction mixture is evaporated to dryness at 40° C leaving a residue which is dissolved in 100 ml of water. The water mixture is extracted three times with 50 ml of diethyl ether. The ether extracts are combined, washed with water, dried with magnesium sulfate and the solvent is evaporated to give a mixture of 25-fluoro1α-hydroxycholesteryl-3-tosylate and 25-fluoro-1α-tosylcholesterol. 25-Fluoro-1α-hydroxycholesteryl-3-tosylate can be separated from 25-fluoro-1α-tosylcholesterol by chromatographing the mixture on a silica gel column using a solvent of petroleum ether and diethyl ether.

B. 3β,25-Difluoro-1α-hydroxycholest-5-ene

25-Fluoro-1α-hydroxycholesteryl-3-tosylate (0.01 mole) prepared according to 4A above is dissolved in 100 ml of dry tetrahydrofuran and refluxed with potassium fluoride (0.4 mole) with stirring for 2 days. The reaction mixture is filtered and the filtrate is evaporated to dryness to give crude 3β,25-difluoro-1α-hydroxycholest-5-ene. 3β,25-Difluoro-1α-hydroxycholest-5-ene can be purifed by chromatographing the crude product on a silica gel column using a solvent of petroleum ether and diethyl ether.

C. 3β,25-Difluoro-1α-hydroxy-3-desoxycholecalciferol

3β,25-Difluoro-1α-hydroxycholest-5-ene prepared according to 4B above is acetylated using the procedure of 1F above to produce 1α-acetoxy-3β,25-difluorocholest-5-ene; 1α-acetoxy-3β,25-difluorocholest-5-ene is brominated using the procedure of 1G above to produce 1α-acetoxy-7-bromo-3β,25-difluorocholest-5-ene; 1α-acetoxy-7-bromo-3β,25-difluorocholest-5-ene is dehydrobrominated using the procedure of 1H above to produce 1α-acetoxy-3β,25-difluoro-5,7-cholestadiene; 1α-acetoxy-3β,25-difluoro-5,7-cholestadiene is irradiated using the procedure of 1I above to produce 1α-acetoxy-3β,25-difluoro-5(10),6,8-trienyl-9,10-seco-cholestene; 1α-acetoxy-3β-difluoro-5(10),6,8-trienyl-9,10-secocholestene is isomerized using the procedure of 1J above to produce 1α-acetoxy-3β,25-difluoro-3-desoxycholecalciferol and 1α-aceotxy-3β,25-difluoro-3-desoxycholecalciferol is saponified using the procedure of 1K above to produce 3β,25-difluoro-1α-hydroxy-3-desoxycholecalciferol.

EXAMPLE 5

25-Fluoro-1α,24-dihydroxycholecalciferol

A. 24,25-Epoxydesmosteryl acetate

Desmosteryl acetate (0.01 mole) and m-chloroperbenzoic acid (0.01 mole) are stirred together in 100 ml. of dry chloroform at 0° C. for 100 minutes. The solution is extracted with saturated aqueous sodium bicarbonate and separated. The chloroform layer is dried with anhydrous magnesium sulfate, filtered and the filtrate evaporated to give crude 24,25-epoxydesmosteryl acetate. 24,25-Epoxydesmosteryl acetate can be purified by chromatographing the crude product on a silica gel column using a solvent of diethyl ether and petroleum ether.

B. 5,6-Dibromo-24,25-epoxydesmosteryl acetate 24,25-Epoxydesmosteryl acetate (0.01 mole) prepared according to 5A above is stirred in 100 ml of dry tetrahydrofuran and dry acid free bromine (0.011 moles) in 10 ml of dry tetrahydrofuran is run in at 10° C over 30 minutes. Dry nitrogen gas is blown through the organic solvent to remove the hydrogen bromide gas. The product is not isolated, but used as is in the following reaction.

C. 5,6-Dibromo-25-fluoro-24-hydroxycholesteryl acetate 5,6-Dibromo-24,25-epoxydesmosteryl acetate from 5B is reacted with a solution of dry hydrogen fluoride (0.01 mole) in 10 ml of dry tetrahydrofuran using polythene apparatus for a period of 30 minutes at room temperature. Dry nitrogen is bubbled through the reaction mixture to remove any remaining hydrogen fluoride gas and the tetrahydrofuran is removed by evaporation to give 5,6-dibromo-25-fluoro-24-hydroxycholesteryl acetate.

D. 25-Fluoro-24-hydroxycholesteryl acetate

Crude 5,6-Dibromo-25-fluoro-24-hydroxycholesteryl acetate from 5C above is dissolved in 70 ml of glacial acetic acid and 5 g of zinc dust is added intermitently over a period of 45 minutes at room temperature. The reaction mixture is filtered and the filtrate is evaporated to dryness. The residue is taken up into 60 ml of diethyl ether and washed twice with 10 ml of saturated sodium bicarbonate. The organic layer is separated, dried with magnesium sulfate, filtered and evaporated to dryness to give crude 25-fluoro-24-hydroxycholesteryl acetate. 25-Fluoro-24-hydroxycholesteryl acetate can be purified by chromatographing the crude product on a silica gel column using a solvent of diethyl ether and petroleum ether.

E. 25-Fluoro-1α,24-dihydroxycholecalciferol

25-Fluoro-24-hydroxycholesteryl acetate prepared according to 5D above is saponified using the procedure of 1B above to produce 25-fluoro-24-hydroxycholesterol; 25-fluoro-24-hydroxycholesterol is converted into the trienone using the procedure of 1C above to produce 25-fluoro-24-hydroxy-1,4,6-cholestatrien-3-one; 25-fluoro-24-hydroxy-1,4,6-cholestatrien- 3-one is epoxidized using the procedure of 1D above to produce 1,2-epoxy-25-fluoro-24-hydroxy-4,6-cholestadien-3-one; 1,2-epoxy-25-fluoro-24-hydroxy-4,6-cholestadien-3-one is reduced using the procedure of 1E above to produce 25-fluoro-1α,24-hydroxycholesterol; 25-fluoro-1α,24-dihydroxycholesterol is acetylated using the procedure of 1F above to produce 1α,24-diacetoxy-25-fluorocholesteryl acetate; 1α,24-diacetoxy-25-fluorocholesteryl acetate is brominated using the procedure of 1G above to produce 1α,24-diacetoxy-7-bromo-25-fluorocholesteryl acetate; 1α,24-diacetoxy-7-bromo-25-fluorocholesteryl acetate is dehydrobrominated using the procedure of 1H to produce 1α,24-diacetoxy-25-fluoro-7-dehydrocholesteryl acetate; 1α,24-diacetoxy-25-fluoro-7-dehydrocholesteryl acetate is irradiated using the procedures of 1I to produce 1α,24-diacetoxy-25-fluoro-5(10),6,8-trienyl-9,10-secocholesteryl acetate; 1α,24-diacetoxy-25-fluoro-5(10),6,8-trienyl-9,10-secocholesteryl is isomerized using the procedure of 1J to produce 1α,24-diacetoxy-25-fluorocholecalciferol and 1α,24-diacetoxy-25-fluorocholecalciferol is saponified using the procedure of 1K to produce 25-fluoro-1α,24-dihydroxycholecalciferol.

EXAMPLE 6

25-Fluoro-1α,24-dihydroxy-3-desoxycholecalciferol

A. 25-Fluoro-1α,24-dihydroxycholesteryl-3-tosylate and 25-Fluoro-24-hydroxy-1α-tosylcholesterol 25-Fluoro-1α,24-dihydroxycholesterol prepared according to 5E above is tosylated using the procedure of 4A to produce a mixture of 25-fluoro-1α,24-dihydroxycholesteryl-3-tosylate and 25-fluoro-24-hydroxy-1α-tosylcholesterol.

B. 25-Fluoro-1α,24-dihydroxycholest-5-ene

25-Fluoro-1α,24-dihydroxycholesteryl-3-tosylate (0.005 mole) prepared according to 6A above is stirred in 50 ml of dry tetrahydrofuran while fresh lithium aluminum hydride (0.005 mole) is slowly added over 20 minutes under a nitrogen blanket at 5°–10° C. The reaction mixture is warmed up to room temperature over a period of 30 minutes. Ethyl acetate (5 ml) is added slowly. The reaction mixture is evaporated to near dryness and poured into 100 ml of a saturated aqueous ammonium chloride solution. The aqueous solution is extracted three times with 30 ml of diethyl ether. The ether extracts are combined, washed with water, dried with magnesium sulfate and evaporated to give crude 25-fluoro-1α,24-dihydroxycholest-5-ene. 25-Fluoro-1α,24-dihydroxycholest-5-ene can be purified by chromatographing the crude product on a silica gel column using a solvent of petroleum ether and diethyl ether.

C. 25-Fluoro-1α,24-dihydroxy-3-desoxycholecalciferol

25-Fluoro-1α,24-dihydroxycholest-5-ene prepared according to 6B above is acetylated using the procedure of 1F above to produce 1α,24-diacetoxy-25-fluorocholest-5-ene; 1α,24-diacetoxy-25-fluorocholest-5-ene is brominated using the procedure of 1G above to produce 1α,24-diacetoxy-7-bromo-25-fluorocholest-5-ene; 1α,24-diacetoxy-7-bromo-25-fluorocholest-5-ene is dehydrobrominated using the procedure of 1H above to produce 1α,24-diacetoxy-25-fluoro-5,7-cholestadiene; 1α,24-diacetoxy-25-fluoro-5,7-cholestadiene is irradiated using the procedure of 1I above to produce 1α,24-diacetoxy-25-fluoro-5(10),6,8-trienyl-9,10-secocholest-5-ene; 1α,24-diacetoxy-25-fluoro-5(10),6,8-trienyl-9,10-sechcholest-5-ene is isomerized using the procedure of 1J above to produce 1α,24-diacetoxy-25-fluoro-3-desocycholecalciferol and 1α,24-diacetoxy-25-fluoro-3-desoxycholecalciferol is saponified using the procedure of 1K above to produce 25-fluoro-1α,24-dihydroxy-3-desoxycholecalciferol.

EXAMPLE 7

O-Methyl cholecalciferol-25-carbamate

A. 25-Chlorocholesteryl acetate

25-Hydroxycholesteryl acetate (0.01 mole) is refluxed with thionyl chloride (0.1 mole) in 100 ml of dry benzene for 1 hour. The reaction mixture is cooled to room temperature and the solvent and excess thionyl chloride are removed by evaporation to give crude 25-chlorocholesteryl acetate.

B. 25-Isocyanatocholesteryl acetate

25-Chlorocholesteryl acetate (0.01 mole) prepared according to 7A above is dissolved in 100 ml of dimethylformamide and heated with stirring for 2 hours at 100° C with sodium isocyanate (0.03 mole). The reaction mixture is cooled to room temperature and 100 ml of water is added. The reaction mixture is extracted twice with 75 ml of diethyl ether. The ether extracts are combined, washed with 30 ml of water, dried with magnesium sulfate, filtered and the filtrate evaporated to give crude 25-isocyanatocholesteryl acetate. 25-Isocyanatocholesteryl acetate can be purified by chromatographing the crude product on a silica gel column using a solvent of petroleum ether and diethyl ether.

C. O-Methyl 3-acetoxycholesteryl-25-carbamate

25-Isocyanotocholesteryl acetate (0.01 mole) prepared according to 7B is dissovled in 100 ml of dry methanol and refluxed for 2 hours and the excess methanol is allowed to evaporate to give crude O-methyl 3-acetoxycholesteryl-25-carbamate. O-Methyl 3-acetoxycholesteryl-25-carbamate can be purified by chromatographing the crude product on a silica gel column using a solvent of petroleum ether and diethyl ether.

D. O-Methyl cholecalciferol-25-carbamate

O-Methyl 3-acetoxycholesteryl-25-carbamate prepared according to 7C above is brominated using the procedure of 1G above to produce O-methyl 3-acetoxy-7-bromocholesteryl-25-carbamate; O-methyl 3-acetoxy-7-bromocholesteryl-25-carbamate is dehydrobrominiated using the procedure of 1H above to produce O-methyl 3-acetoxy-7-dehydrocholesteryl-25-carbamate; O-methyl 3-acetoxy-7-dehydrocholesteryl-25-carbamate is irradiated using the product of 1I above to produce O-methyl 3-acetoxy-5(10),6,8-trienyl-9,10-secocholesteryl-25-carbamate; O-methyl 3-acetoxy-5(10),6,8-trienyl-9,10-secocholesteryl-25-carbamate is isomerized using the procedure of 1J above to produce O-methyl 3-acetoxycholecalciferol-25-carbamate; O-methyl 3-acetoxycholecalciferol-25-carbamate is saponified using the procedure of 1K above to produce O-methyl cholecalciferol-25-carbamate.

EXAMPLE 8

24,25-Difluoro-1α-hydroxycholecalciferol

A. 5,6-Dibromodesmosteryl acetate

Desmosteryl acetate is brominated using the procedure of 5B above to produce 5,6-dibromodesmosteryl acetate.

B. 24,25-Difluoro-5,6-dibromodesmosteryl acetate 5,6-Dibromodesmosteryl acetate (0.01 mole) in 20 ml of dry Freon 11 ® is fluorinated using the procedure of Merritt and Johnson (*J. Org. Chem.*, 31, p. 1859, 1966) by bubbling dry fluorine gas into the reaction mixture at −78° C for 10 minutes in the presence of 3.0 g of molecular sieves (4A). The reaction mixture is flushed by bubbling argon gas through the mixture for 10 minutes, filtered to remove the molecular sieves and evaporated to dryness to give 24,25-difluoro-5,6-dibromodesmosteryl acetate. 24,25-difluoro-5,6-dibromodesmosteryl acetate can be purified by chromatographing the crude product on a silica gel column using a solvent of petroleum ether and diethyl ether.

C. 24,25-Difluoro-1α-hydroxycholecalciferol 24,25-Difluoro-5,6-dibromodesmosteryl acetate prepared according to 8B above is debrominiated using the procedure of 5D above to produce 24,25-difluorocholesteryl acetate; 24,25-difluorocholesteryl acetate is saponified using the procedure of 1B above to produce 24,25-difluorocholesterol; 24,25-difluorocholesterol is converted to the trienone using the procedure of 1C above to produce 24,25-difluoro-1,4,6-cholestatrien-3-one; 24,25-difluoro-1,4,6-cholestatrien-3-one is epoxidized using the procedure of 1D above to produce 1,2-epoxy-24,25-difuloro-4,6-cholestadien-3-one; 1,2-epoxy-24,25-difluoro-4,6-cholestadien-3-one is reduced using the procedure of 1E above to produce 24,25-difluoro-1α-hydroxycholesterol; 24,25-difluoro-1α-hydroxycholesterol is acetylated using the procedure of 1F above to produce 1α-acetoxy-24,25-difluorocholesteryl acetate; 1α-acetoxy-24,25-difluorocholesteryl acetate is brominated using the procedure of 1G above to produce 1α-acetoxy-7-bromo-24,25-difluorocholesteryl acetate, 1α-acetoxy-7-bromo-24,25-difluorocholesteryl acetate is dehydrobrominated using the procedure of 1H above to produce 1α-acetoxy-7-dehydro-24,25-difluorocholesteryl acetate; 1α-acetoxy-7-dehydro-24,25-difluorocholesteryl acetate is irradiated using the procedure of 1I above to produce 1α-acetoxy-24,25-difluoro-5(10),6,8-trienyl-9,10-seco-cholesteryl acetate; 1α-acetoxy-24,25-difluoro-5(10),6,8-trienyl-9,10-secocholesteryl acetate is isomerized using the procedure of 1J above to produce 1α-acetoxy-24,25-difluorocholecalciferol acetate; and 1α-acetoxy-24,25-difluorocholecalciferol acetate is saponified using the procedure of 1K above to produce 24,25-difluoro-1α-hydroxycholecalciferol.

EXAMPLE 9

25-Fluorocholecalciferol

A. 3β,25-Dibenzoyloxycholest-5-ene

Heat 2.9 gm. (7.2 mmole) of 25-hydroxycholesterol with 2.1 ml. (18 mmole) of benzoyl chloride in 30 ml. of pyridine at 70°–80° C. for 4 hours. Add an additional 1.4 ml. (12 mmole) of benzoyl chloride and continue heating at 75°–80° C. for 1 hour. Pour the reaction mixture into ice-water mixture (1:1, 500 gm.) Stir for 1 hour, separate the precipitate and wash with ice-water. Recrystalize from acetone. Dissolve the crude product (3.8 gm.) in methylene chloride-hexane (3:2, 40 ml.) and pass the solution through a silica gel column (120 gm.). Elute the column with 800 ml. methylene chloride-hexane (5:1) followed by 800 ml. methylene chloridehexane (10:1). Combine the fractions and concentrate to a residue. Recrystalize from acetone to obtain the pure product (3.32 gm., m.p. 130°–132° C.).

B. 7-Bromo-3 β,25-dibenzoyloxycholest-5-ene

To a boiling solution of 2.02 gm. of 3β,25-dibenzoyloxycholest- 5-ene (3.3 mmole) in 90 ml. of hexane, and 720 mg. (2.52 mmole) of dibromo-dimethylhydantoin. Reflux for 30 minutes, cool to room temperature, filter and wash with 2 ml. of carbontetrachloride. Concentrate the combined filtrate to dryness to obtain the title product. (2.3 gm.)

C. 3β,25-Dibenzoyloxycholesta-5,7-diene

To a refluxing solution of 4.2 ml. of trimethylphosphite in 90 ml. of xylene under a nitrogen atmosphere, add a solution of the crude 7-bromo compound obtained above (2.3 gm.) in 50 ml. of xylene over a 15 minute period. Heat the mixture under reflux for 65 minutes and distill off approximately 10 ml. of the solvent. Concentrate the reaction mixture in vacuo and pump the residue to a constant weight (2.05 gm.). The residue, containing approximately 29% of the desired product by U.V. analysis, was dissolved in 100 ml. of methylene chloride and used in the next step.

D. 3α,25-Dibenzoyloxy-4′-phenyl-5α,8α-[1′,2′]-1′,2′4′-triazolidinocholest-6-ene-3′,5′-dione To the solution of the diene obtained above, add 4-phenyldehydrourazole crystals in portions until the red color presists. Concentrate the reaction mixture to dryness to obtain the crude adduct (2.67 gml). Dissolve the crude adduct in chloroform (20 ml.) and chromatograph on silica gel (100 gm.) eluting with chloroform. Concentrate the eluates to dryness and triturate with ether to purify the product. Further purify the product by preparative thin layer chromatography on silica gel plates (1000µ) developing with 20% acetone in hexane. Extract the pure product (desired zone) with 10% acetone in chloroform. Evaporate the extract to a residue and triturate with ether to obtain the pure product (m.p. 206°–207° C., sinters at 204° C., 123 mg.).

E. 25-Hydroxy-7-dehydrocholesterol

To a stirred suspension of 200 mg. of lithium aluminum hydride in 20 ml. of tetrahydrofuran, add a solution of 100 mg. of the pure cyclo adduct obtained in Step D above in 20 ml. of tetrahydrofuran at room temperature. Heat under reflux for 1 hour and cool to room temperature. Add 10 ml. of saturated sodium sulfate to destroy excess lityium aluminum hydride. Separate the organic layer and wash with aqueous sodium sulfate solution. Remove the solvent to obtain the desired diol diene (85 mg.).

F. 25-Hydroxy-7-dehydrocholesteryl-3-acetate

Dissolve the crude 25-hydroxy-7-dehydrocholesterol of Step E in 15 ml. of pyridine at 0°–5° C. and add 2 ml. of acetic anhydride dropwise. Stir at room temperature overnight. Concentrate the mixture in vacuo at room temperature to a residue. Purify by preparative thin layer chromatography on 2 plates (1000µ silica gel) developing with 6% ethyl acetate in chloroform. Extract the desired zone with the chloroform-ethyl acetate mixture and remove the solvent to obtain the title product (48 mg.).

G-1. 25-Fluoro-7-dehydrocholesteryl-3-acetate

To a stirred solution of the 25-hydroxy-7-dehydrocholesteryl-3-acetate of Step F in 5 ml. of methylene chloride, add 1.1 ml. of TRI-SIL reagent. Stir the mixture at room temperature for 1 hour. Add 0.2 ml. of phenyltetrafluorophosphorane and continue stirring at ambient temperature for 1 hour. Stir the reaction mixture with ice-water and separate the layers. Wash the aqueous layer with methylene chloride and concentrate the combined organic phases to dryness. Purify the residue by preparative thin layer chromatography on 2 silica gel plates (1000μ) developing with 5% acetone in hexane. Extract the desired zone with methylene chlorideacetone (1:1). Concentrate to dryness and recrystallize from acetone to obtain the title product (m.p. 131°–134° C.).

G–2. 25-Fluoro-7-dehydrocholesteryl-3-acetate

Add a solution of 223 mg. of 25-hydroxy-7-dehydrocholesterol-3-acetate in 5 ml. of methylene chloride to a cold solution of 0.09 ml. of diethylaminosulfurtrifluoride in 10 ml. of methylene chloride at 78° C. under nitrogen over a 15 minute period. Allow the mixture to warm to room temperature and, after 1 hour, wash the mixture with ice-water. Separate and dry the organic layer and concentrate to dryness. Purify the crude product by preparative thin layer chromatography on 2 plates (silica gel, 2000μ) developing with 7.5% acetone in hexane. Extract the desired zone with 10% ethyl acetate in methylene chloride. Remove the solvent to give the desired product. Further purify by recrystallization from acetone (m.p. 130°–133° C., mixed m.p. with product of Step G-1, 130°–133° C., NMR superimposable with Sample G-1).

H. 25-Fluoro-5-(10),6,8-trienyl-9,10-secocholesteryl-3-acetate (25-Fluoroprevitamin $D_3$ Acetate Irradiate 450 mg. of 25-fluoro-7-dehydrocholesteryl-3-acetate from the preceding step in 600 ml. of ether at 0° to 5° C. under a nitrogen atmosphere for 15 minutes using a Hanovia medium pressure quartz mercury vapor lamp (450 watt). Add 10 mg. of 9-fluorenone to the photolysis mixture and continue irradiation at 0° to 5° C. under nitrogen for an additional 10 minutes. Concentrate to dryness. Purify by preparative thin layer chromatography on 2000μ silica gel plates and develop with 7.5% acetone in hexane. Extract the desired zones with 5% ethyl acetate in chloroform at 0° to 5° C. under nitrogen. Remove the solvent in vacuo to obtain the desired product.

I. 25-Fluorocholecalciferol-3-acetate

Reflux 280 mg. of 25-fluoro-previtamin $D_3$ acetate in 15 ml. of isooctane for 2 ¼ hours under a nitrogen atmosphere. Concentrate in vacuo to a residue. Purify by preparative thin layer chromatography on 2000μ silica gel plates. Develope with 9% acetone in hexane. Extract the desired zone with 5% methanol in chloroform and concentrate in vacuo to obtain the desired product. Recrystallization from 95% aqueous ethanol gives extra-fine crystalls in the cold. Collection of the crystalls gives a semi-solid at room temperature.

J. 25-Fluorocholecalciferol

To a solution of 45 mg. of 25-fluorocholecalciferol-3-acetate in 1 ml. of tetrahydrofuran and 1 ml. of ethanol at 0° to 5° C. under a nitrogen atmosphere, add 0.2 ml. of 2.5 N Sodium hydroxide. Allow the mixture to stand at room temperature for 17 hours. Purify by low temperature thin layer chromatography techniques on silica gel plates (1000μ). Develope with 20% acetone in hexane. Extract the desired zone with 5% ethyl acetate in chloroform. Evaporate the solvent to obtain the title product (15 mg.).

EXAMPLE 10

25-Fluorocholecalciferol — 3,5-dinitrobenzoate

Treat a cold solution of 10 mg. of 25-fluorocholecalciferol in 0.8 ml. of methylene chloride and pyridine (0.5 ml.) at 0°–5° C. with 20 mg. of 3,5-dinitro-benzoylchloride. Hold the solution under a nitrogen atmosphere at room temperature for 4 hours. Concentrate the reaction mixture in vacuo at toom temperature and quench with ice-water. Collect the precipitate, wash with diluted cold bicarbonate, water and dry. Recrystallize from aqueous ethanol to obtain the title product (m.p. 132°–135° C.).

EXAMPLE 11

25-Fluorotachysterol$_3$

A. 25-Fluororachysteryl$_3$-3-acetate

To a solution of 40 mg. of 25-fluoroprevitamin $D_3$-3-acetate (prepared according to Example 8 H) in 10 ml. of hexane at 0°–5° C. under a nitrogen atmosphere, add a solution of 1.2 gm. of iodine in 1 ml. of hexane. Allow the mixture to warm to room temperature. Concentrate the mixture in vacuo to a residue and flush with choroform. Remove the solvent to give the desired product (40 mg.).

B. 25-Fluorotachysterol$_3$

To a solution of 40 mg. of 25-fluorotachysteryl$_3$-3-acetate in 1 ml. of tetrahydrofuran and 1 ml. of ethanol under a nitrogen atmosphere, add 0.25 ml. of 2.5 N sodium hydroxide. Stir in the dark at room temperature for 18 hours. Apply the reaction mixture to 8% silver nitrate impregnated silica gel plates (1000μ) at 5° C. in the dark and develop with 15% acetone in hexane. Extract the desired zone with 5% ethanol in chloroform. Remove the solvent to obtain the desired product (10 mg.).

EXAMPLE 12

25-Fluoro-9,10-dihydrotachysterol$_3$

To a well stirred mixture of 1 gm. of sodium metal and 30 ml. of xylene which has been heated to reflux under nitrogen is added a solution of 400 mg. of 25-fluorotackysterol$_3$ in 10 ml. of xylene. There is then added dropwise 20 ml. of t-amyl alcohol over a period of 1 hour after which the reaction mixture is heated for an additional hour. The mixture is then cooled and any excess sodium is consumed by the addition of the solvent in vacuo, the residue is taken up between 50 m of ether and 50 ml. of water. The ether layer is separated, dried and concentrated in vacuo. Purify by preparative thin layer chromatography of the residue on silver nitrate impregnated silica gel at 5° C. in the dark developing with 15% acetone in hexane. Extract the desired zone with 5% ethanol in chloroform and remove the solvent to obtain the title product.

EXAMPLE 13

25-Fluorocholesteryl-3-acetate

To a mixture of 1.0 gm. of diethylaminosulfurtrifluoride and 30 ml. of methylene chloride which has been cooled in a DRY ICE/acetone bath, add slowly a solution of 2.225 gm. of 25-hydroxycholesteryl-3-acetate in 20 ml. of methylene chloride. The reaction mixture is stirred for ½ hour at −60° C. and then allowed to warm to −20° C. The mixture is quenched with a solution of 5 gm. of sodium bicarbonate in 50 ml. of water. The organic layer is separated, washed with water, dried and concentrated in vacuo. The residue is chromatographed on 300 gm. of silica gel. Elution with benzene (25–50%) in petroleum ether gives the title compound.

What is claimed is:

1. A compound of the formulae:

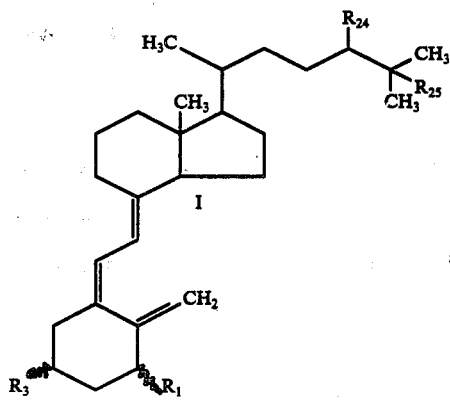

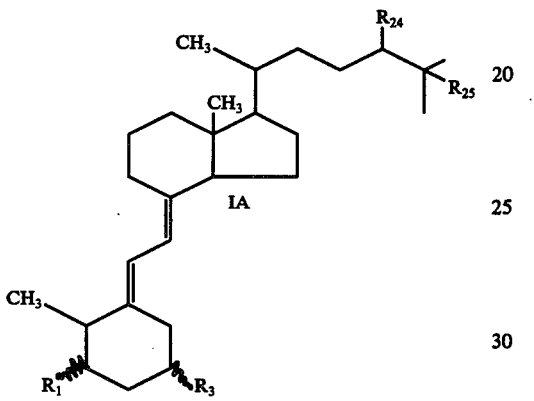

wherein $R_1$ is hydrogen, hydroxy, $C_{1-5}$alkanoyloxy, substituted $C_{1-5}$alkanoyloxy, branched $C_{3-5}$alkanoyloxy, benzoyloxy or p-nitro-benzyloxy, $R_3$, $R_{24}$ and $R_{25}$ are hydrogen, hydroxy, $C_{1-5}$alkanoyloxy, substituted $C_{1-5}$alkanoyloxy, branched $C_{3-5}$alkanoyloxy, benzoyloxy, p-nitro-benzyloxy halo or O—$C_{1-5}$alkyl carbamate with the proviso that $R_{25}$ is halo or O—$C_{1-5}$akyl carbamate.

2. The compounds of claim 1 wherein $R_1$, $R_3$ and $R_{24}$ are hydrogen or hydroxy.

3. The compounds of claim 2 wherein $R_{25}$ is fluoro.

4. 25-Fluoro-1α-hydroxycholecalciferol according to claim 3.

5. 25-Fluorocholecalciferol according to claim 3.

6. O-Methyl cholecalciferol-25-carbamate according to claim 2.

7. 25-Fluoro-1α-hydroxy-9,10-dihydrotachysterol₃ according to claim 3.

8. 25-Fluoro-9,10-dihydrotachysterol₃ according to claim 3.

9. O-Methyl-9,10-dihydrotachysterol₃-carbamate according to claim 2.

10. A pharmaceutical composition comprising a non-toxic pharmaceutically acceptable carrier and a compound of the formulae:

wherein $R_1$, is hydrogen, hydroxy, $C_{1-5}$alkanoyloxy, substituted $C_{1-5}$alkanoyloxy, branched $C_{3-5}$alkanoyloxy, benzoyloxy or p-nitro-benzyloxy, $R_3$, $R_{24}$ and $R_{25}$ are hydrogen, hydroxy, $C_{1-5}$alkanoyloxy, substituted $C_{1-5}$alkanoyloxy, branched $C_{3-5}$alkanoyloxy, benzoyloxy, p-nitro-benzyloxy, halo or O—$C_{1-5}$alkyl carbamate with the proviso that $R_{25}$ is halo or O—$C_{1-5}$alkyl carbamate.

11. A method of treating steroid-induced osteoporosis, senile osteoporosis and secondary hyderparathyroidism which comprises administering to a patient a therapeutically effective amount of a compound of the formulae:

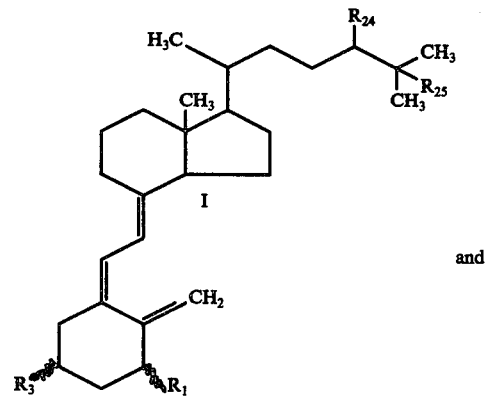

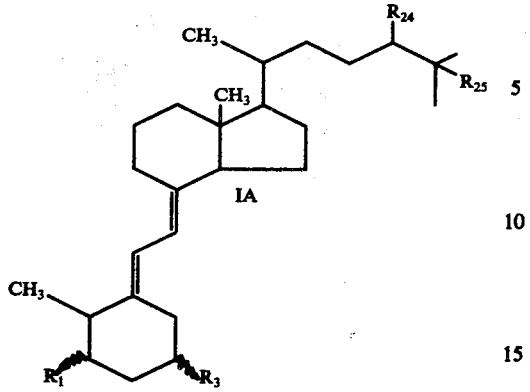

wherein

R₁ is hydrogen, hydroxy, $C_{1-5}$alkanoyloxy, substituted $C_{1-5}$alkanoyloxy, branched $C_{3-5}$alkanoyloxy, benzoyloxy or p-nitro-benzoyloxy, R₃, R₂₄ and R₂₅ are hydrogen, hydroxy, $C_{1-5}$alkanoyloxy, substituted $C_{1-5}$alkanoyloxy, branched $C_{3-5}$alkanoyloxy, benzoyloxy, p-nitro-benzoyloxy, halo or O—$C_{1-5}$alkyl carbamate with the proviso that R₂₅ is halo or O—$C_{1-5}$alkyl carbamate.

* * * * *

UNITED STATES PATENT AND TRADEMARK OFFICE
CERTIFICATE OF CORRECTION

PATENT NO. : 4,069,321
DATED : January 17, 1978
INVENTOR(S) : Howard Jones; Shu Shu Yang and David P. Jacobus It is certified that error appears in the above-identified patent and that said Letters Patent are hereby corrected as shown below:

Column 1, the structural formula should read as follows:

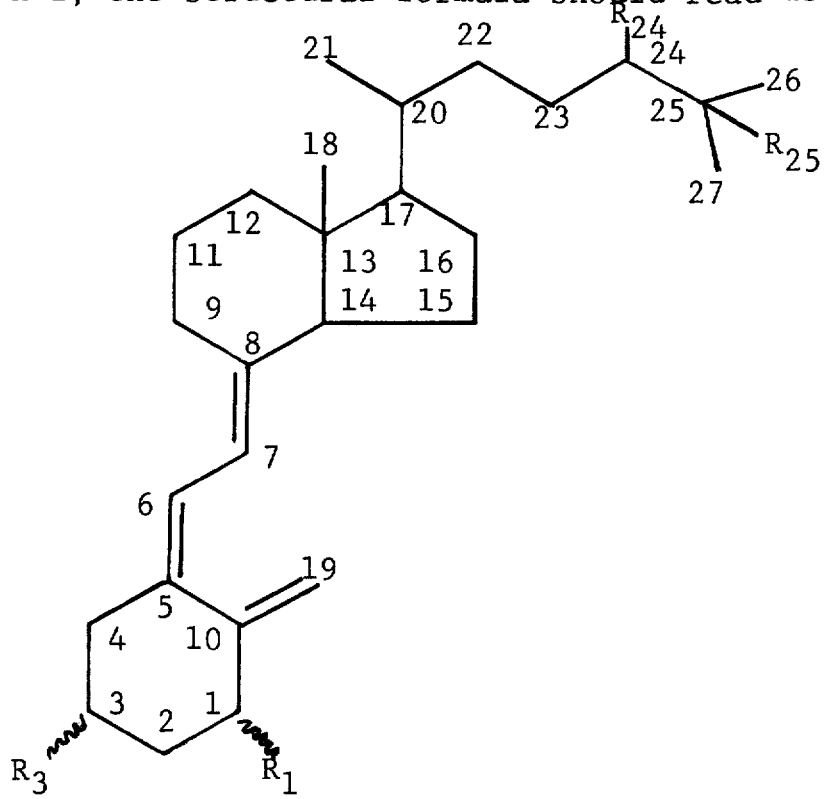

UNITED STATES PATENT AND TRADEMARK OFFICE
CERTIFICATE OF CORRECTION

PATENT NO. : 4,069,321
DATED : January 17, 1978

Page 2 of 3

INVENTOR(S) : Howard Jones; Shu Shu Yang and David P. Jacobus

It is certified that error appears in the above-identified patent and that said Letters Patent are hereby corrected as shown below:

Column 2, the structural formula should read as follows:

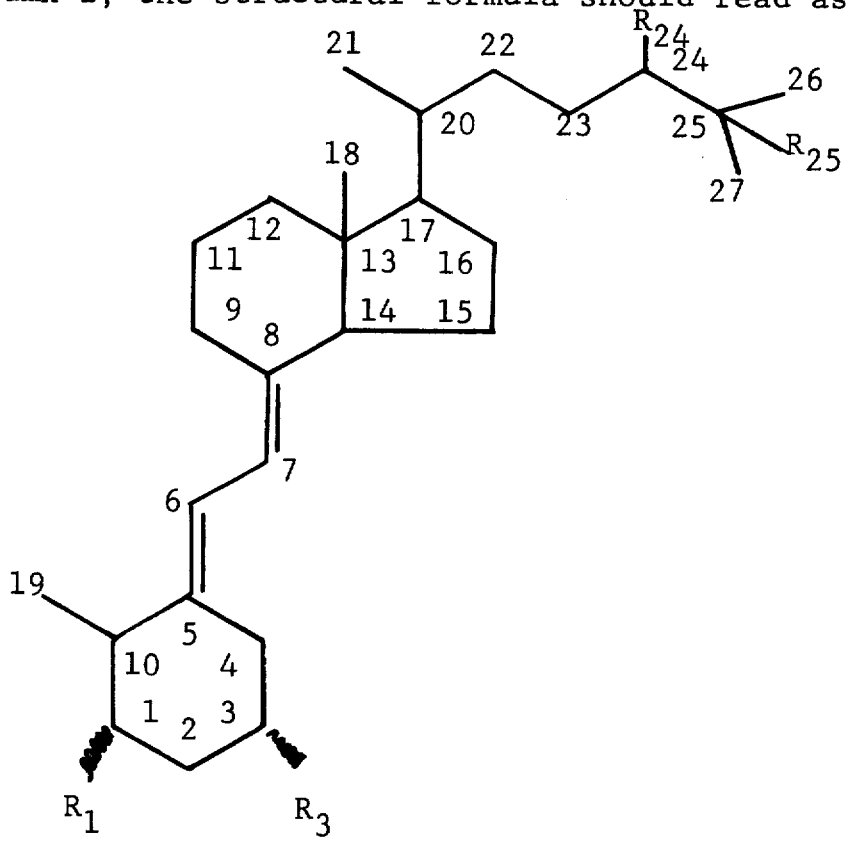

UNITED STATES PATENT OFFICE
CERTIFICATE OF CORRECTION

PATENT NO. : 4,069,321
DATED : January 17, 1978
INVENTOR(S) : Howard Jones; Shu Shu Yang and David P. Jacobus It is certified that error appears in the above-identified patent and that said Letters Patent are hereby corrected as shown below:

Column 7, line 36, "75°1C." should read -- 75°C. --.

Column 13, line 40, "25-fluoro1α-hydroxycholeste-" should read -- 25-fluoro-1α-hydroxycholeste- --.

Column 14, line 38, "5B is" should read -- 5B above is --.

Column 21, line 63, "O-Methyl-9,10-dihydrotachysterol$_3$-carbamate" should read -- O-Methyl-9,10-dihydrotachysterol$_3$-25-carbamate --.

Signed and Sealed this

Sixteenth Day of May 1978

[SEAL]

Attest:

RUTH C. MASON
Attesting Officer

LUTRELLE F. PARKER
Acting Commissioner of Patents and Trademarks